(12) United States Patent
Honda et al.

(10) Patent No.: US 10,021,312 B2
(45) Date of Patent: Jul. 10, 2018

(54) ENDOSCOPE SYSTEM AND METHOD FOR OPERATING ENDOSCOPE SYSTEM (71) Applicant: OLYMPUS CORPORATION, Tokyo (JP)

(72) Inventors: Kazuki Honda, Higashiyamato (JP); Yasuhito Kura, Hachioji (JP); Takeo Suzuki, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 15/258,563

(22) Filed: Sep. 7, 2016

(65) Prior Publication Data

US 2016/0381273 A1 Dec. 29, 2016

Related U.S. Application Data (63) Continuation of application No. PCT/JP2015/075216, filed on Sep. 4, 2015.

(30) Foreign Application Priority Data

Sep. 9, 2014 (JP) .................................. 2014-183511

(51) Int. Cl.
*H04N 9/47* (2006.01)
*H04N 7/18* (2006.01)
(Continued)

(52) U.S. Cl.
CPC ............. *H04N 5/2351* (2013.01); *A61B 1/04* (2013.01); *G02B 23/24* (2013.01); *H04N 5/2256* (2013.01);
(Continued)

(58) Field of Classification Search
CPC .... H04N 5/2351; H04N 5/243; H04N 5/2354; H04N 5/2256; H04N 2005/2255; H04N 5/23293; G02B 23/24; A61B 1/04
(Continued)

(56) References Cited

U.S. PATENT DOCUMENTS

2001/0019363 A1 9/2001 Katta et al.
2004/0092792 A1* 5/2004 Kobayashi ............. A61B 1/018
600/101
(Continued)

FOREIGN PATENT DOCUMENTS

CN 101631200 A 1/2010
CN 102469912 A 5/2012
(Continued)

OTHER PUBLICATIONS

International Search Report dated Dec. 1, 2015 issued in PCT/JP2015/075216.
(Continued)

*Primary Examiner* — Jared Walker
(74) *Attorney, Agent, or Firm* — Scully, Scott, Murphy & Presser, P.C.

(57) ABSTRACT

An endoscope system includes: an image configuring portion configured to configure a first image and a second image based on image pickup signals corresponding to different areas in a same subject; a luminance detecting portion configured to detect luminances of the first and second images; and a luminance control portion adjusting, for areas obtained by dividing each of the first and second images as units, the luminance of at least one of the images so that a luminance difference between two areas where the first image and the second image adjoin each other becomes equal to or smaller than a threshold.

15 Claims, 8 Drawing Sheets (51) Int. Cl.
*A61B 1/04* (2006.01)
*H04N 5/235* (2006.01)
*G02B 23/24* (2006.01)
*H04N 5/225* (2006.01)
*H04N 5/243* (2006.01)
*H04N 5/232* (2006.01)

(52) U.S. Cl.
CPC ........... *H04N 5/2354* (2013.01); *H04N 5/243* (2013.01); *H04N 5/23293* (2013.01); *H04N 2005/2255* (2013.01)

(58) Field of Classification Search
USPC .......................................................... 348/69
See application file for complete search history.

(56) References Cited

U.S. PATENT DOCUMENTS

| | | | |
|---|---|---|---|
| 2013/0041226 A1* | 2/2013 | McDowall | A61B 1/00009 600/166 |
| 2014/0092215 A1 | 4/2014 | Hayama | |
| 2014/0204187 A1 | 7/2014 | Sasaki et al. | |
| 2014/0218479 A1 | 8/2014 | Nishimura | |

FOREIGN PATENT DOCUMENTS

| | | |
|---|---|---|
| EP | 1471482 A1 | 10/2004 |
| EP | 2 759 248 A2 | 7/2014 |
| EP | 2762059 A1 | 8/2014 |
| JP | 2001-320616 A | 11/2001 |
| JP | 2002-017667 A | 1/2002 |
| JP | 2003-179785 A | 6/2003 |
| JP | 2007-190060 A | 8/2007 |
| JP | 4782900 B2 | 9/2011 |
| JP | 2012-157577 A | 8/2012 |
| JP | 2013-066646 A | 4/2013 |
| JP | 2013-179785 A | 9/2013 |
| JP | 2013-542467 A | 11/2013 |
| WO | WO2011055613 A1 | 5/2011 |
| WO | WO 2013/047215 A1 | 4/2013 |

OTHER PUBLICATIONS

Extended Supplementary European Search Report dated Nov. 2, 2017 in European Patent Application No. 15 83 9553.3.

* cited by examiner

ENDOSCOPE SYSTEM AND METHOD FOR OPERATING ENDOSCOPE SYSTEM

CROSS REFERENCE TO RELATED APPLICATION

This application is a continuation application of PCT/JP2015/075216 filed on Sep. 4, 2015 and claims benefit of Japanese Application No. 2014-183511 filed in Japan on Sep. 9, 2014, the entire contents of which are incorporated herein by this reference.

BACKGROUND OF THE INVENTION

1. Field of the Invention

The present invention relates to an endoscope system for acquiring a first image and a second image of different areas in a same subject, and a method for operating the endoscope system.

2. Description of the Related Art

Recently, a wide angle endoscope having a front-view observation optical system and a lateral-view observation optical system has been proposed in order to make it possible to observe a wider range.

Such wide angle endoscopes include a type in which a front-view subject image through a front-view observation window and a lateral-view subject image through a lateral-view observation window are formed on one image pickup device, for example, as described in Japanese Patent No. 4782900, type in which a camera including an optical system and an image pickup device which are combined is provided for each of front-view and lateral-view, as described in Japanese Patent Application Laid-Open Publication No. 2013-542467 (International Publication No. 2012/056453), and others.

Such a wide angle endoscope having the front-view observation optical system and the lateral-view observation optical system is provided with an illumination portion configured to radiate light forward and an illumination portion configured to radiate light laterally, separately. Furthermore, some wide angle endoscopes can also adjust an amount of light radiated forward and an amount of light radiated laterally, separately.

By the way, in a case of radiating illuminating light to a subject, a state occurs in which illuminance is high in a proximal part and low in a remote part, and the proximal part and the remote part are observed brighter and darker, respectively. More specifically, in a case of observing, for example, a luminal subject using a wide angle endoscope, it may happen that a central part of an observation site by front-view becomes a remote part in an axial direction of a lumen and becomes dark, and an observation site by lateral-view becomes a proximal part of a luminal inner wall and becomes bright. Furthermore, in a case where the endoscope comes close to a left side wall in the lumen, for example, a subject distance differs on left and right sides, and, therefore, such an image is obtained that not only a left lateral field of view and a right lateral field of view become bright and dark, respectively, but also a left side and right side of a forward field of view become bright and dark, respectively.

When brightness of an image becomes imbalanced as described above, an endoscope capable of adjusting an amount of illuminating light for each field-of-view direction as described above, performs amount-of-light control for avoiding brightness imbalance, for example, by increasing an amount of light radiated in a right side direction.

For example, International Publication No. 2011/055613 describes an endoscope system in which brightness of a front-view field-of-view image and brightness of a lateral-view field-of-view image are separately detected, and, based on a detection result, a light source apparatus is controlled so that one of the field-of-view images reaches a brightness target value suitable for observation.

Further, Japanese Patent Application Laid-Open Publication No. 2003-179785 describes a technique in which, in an image photographing apparatus for performing photographing of a wide angle image and photographing of an enlarged image, an amplification factor of each image signal is set so that the wide angle image and the enlarged image are displayed with same brightness.

SUMMARY OF THE INVENTION

An endoscope system according to a certain aspect of the present invention includes: an image configuring portion configured to configure a first image and a second image based on image pickup signals corresponding to different areas in a same subject; a luminance detecting portion configured to detect luminances in the first image and the second image; and a luminance control portion configured to divide each of the first image and the second image arranged adjoining each other into a plurality of areas and adjust the luminance of at least one of the first image and the second image so that a luminance difference between two of the areas where the first image and the second image adjoin each other becomes equal to or smaller than a threshold.

A method for operating an endoscope system according to an aspect of the present invention is a method for operating an endoscope system comprising an illumination portion configured to radiate light to a first area in a subject and a second area in the subject different from the first area; the method comprising the steps of: a first subject image acquiring portion provided in an insertion portion acquiring a first image pickup signal of a first subject image of the first area; a second subject image acquiring portion provided in the insertion portion acquiring a second image pickup signal of a second subject image of the second area; an image configuring portion configuring a first image based on the first image pickup signal and configuring a second image based on the second image pickup signal; a luminance detecting portion detecting each of a luminance of the first image and a luminance of the second image; a luminance control portion dividing each of the first image and the second image arranged adjoining each other into a plurality of areas; and the luminance control portion adjusting, for the divided areas as units, the luminance of at least one of the first image and the second image so that a luminance difference between two of the areas where the first image and the second image adjoin each other becomes equal to or smaller than a threshold.

DETAILED DESCRIPTION OF THE PREFERRED EMBODIMENT(S)

Embodiments of the present invention will be described below with reference to drawings.

First Embodiment

Figure 1:
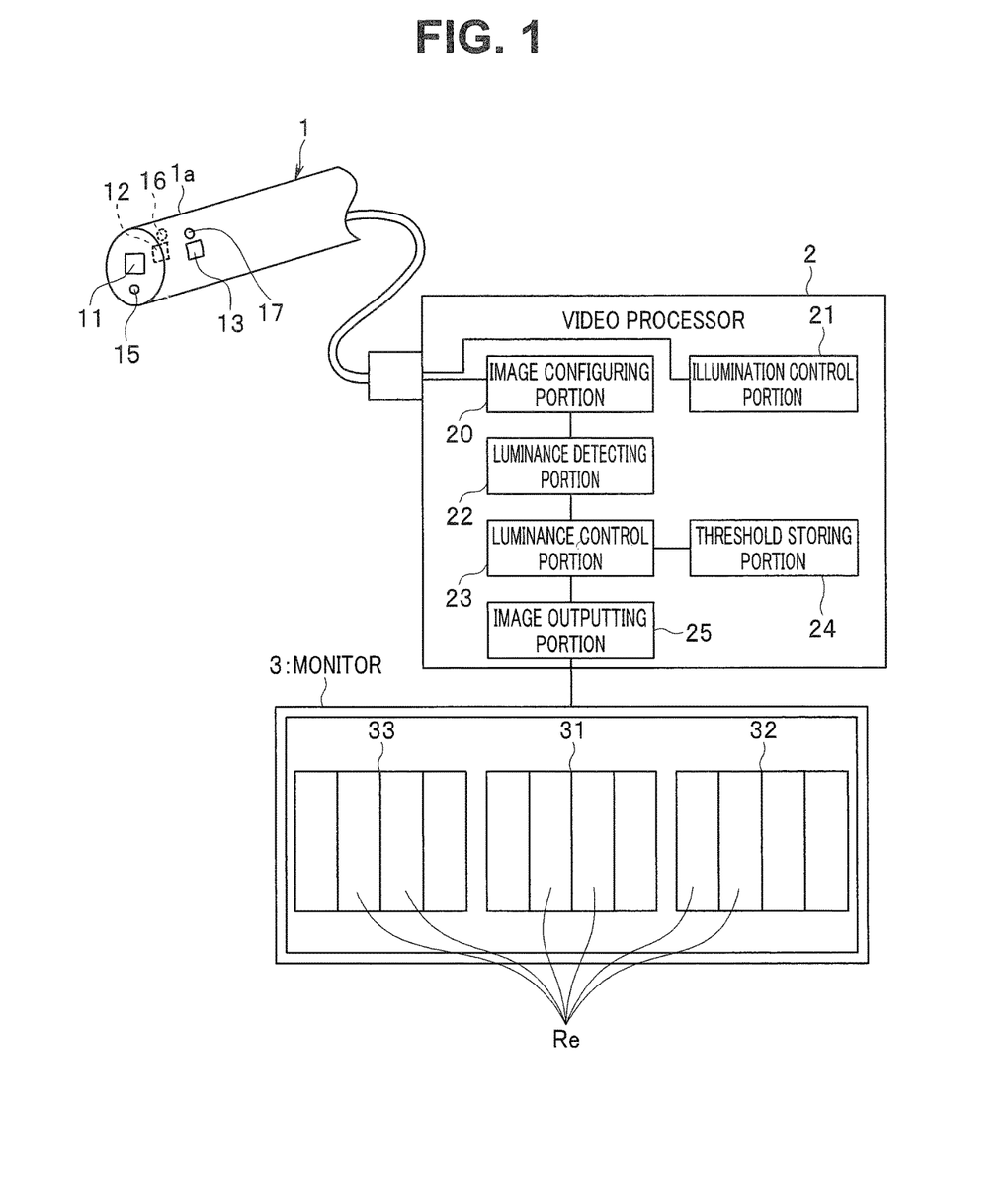
FIG. 1 is a diagram showing a configuration of an endoscope system in a first embodiment of the present invention.

FIGS. 1 to 8 show a first embodiment of the present invention, and FIG. 1 is a diagram showing a configuration of an endoscope system.

As shown in FIG. 1, the endoscope system is provided with an endoscope 1, a video processor 2 and a monitor 3.

The endoscope 1 is configured as an electronic endoscope provided with an insertion portion 1a to be inserted into an inside of a subject. The endoscope 1 is provided with a first subject image acquiring portion provided in the insertion portion 1a and configured to acquire a first image pickup signal of a first subject image (an optical image) of a first area in a subject, a second subject image acquiring portion provided in the insertion portion 1a and configured to acquire a second image pickup signal of a second subject image (an optical image) of a second area in the subject different from the first area, and an illumination portion configured to radiate light to the first and second areas.

More specifically, an example of the first area is an area which includes a forward direction in the subject (a forward field-of-view area), and the first subject image acquiring portion is arranged in a distal end portion of the insertion portion 1a facing forward and includes an image pickup portion 11 (a first image pickup portion) configured to perform photoelectric conversion of the first subject image (optical image) of the first area in the subject, including a forward direction along a longitudinal direction of the insertion portion 1a, to generate a first image pickup signal.

Further, an example of the second area different from the first area is an area which includes a lateral direction of the same subject (a lateral field-of-view area), and the second subject image acquiring portion performs photoelectric conversion of the second subject image (optical image) of the second area in the subject, including a lateral direction crossing the longitudinal direction of the insertion portion 1a to generate a second image pickup signal. More specifically, a plurality of second subject image acquiring portions are arranged at a plurality of angle positions in a circumferential direction of the insertion portion 1a and acquire a plurality of second image pickup signals of a plurality of second subject images. Especially here, the second subject image acquiring portion includes an image pickup portion 12 configured to pick up an image of an area in a right lateral field of view (a second image pickup portion separate from the first image pickup portion) and an image pickup portion 13 configured to pick up an image of an area in a left lateral field of view (a second image pickup portion separate from the first image pickup portion). The right and left lateral fields of view are, for example, two equally divided positions in a circumferential direction with a forward field of view as a center.

Each of the image pickup portions 11 to 13 is configured including an image pickup optical system and an image pickup device and is configured to perform to perform photoelectric conversion of a subject image formed by the image pickup optical system, by the image pickup device to generate an image pickup signal, and output the generated image pickup signal to the video processor 2 electrically connected to the image pickup portions 11 to 13.

Further, as the illumination portion, a first illumination portion configured to radiate light to the first area and a second illumination portion configured to radiate light to the second area are provided. More specifically, an illumination portion 15 configured to radiate light to a range of image pickup by the image pickup portion 11 corresponds to the first illumination portion. Further, an illumination portion 16 configured to radiate light to a range of image pickup by the image pickup portion 12 and an illumination portion 17 configured to radiate light to a range of image pickup by the image pickup portion 13 correspond to the second illumination portion. Therefore, the illumination portion 15 illuminates the forward direction, the illumination portion 16 illuminates the right lateral direction, and the illumination portion 17 illuminates the left lateral direction.

The illumination portions 15, 16 and 17 are configured including a light emitting device such as an LED and configured to adjust respective amounts of light to emit light based on a control signal from an illumination control portion 21 of the video processor 2 to be described later.

Note that, though the right and left lateral directions are shown as examples of lateral directions which the illumination portion illuminates and in which the image pickup portion picks up an image here, an upper lateral direction, a lower lateral direction, an oblique lateral direction or the like may be included instead of or in addition to the right and left lateral directions. Furthermore, any combination of the directions is also possible.

On the other hand, the video processor 2 is provided with an image configuring portion 20, the illumination control portion 21, a luminance detecting portion 22, a luminance control portion 23, a threshold storing portion 24 and an image outputting portion 25.

The image configuring portion 20 configures a first image and second images based on image pickup signals corresponding to different areas in a same subject. The image configuring portion 20 receives a first image pickup signal from the first image pickup portion electrically connected via a signal line 14 to configure the first image (image signal), and receives second image pickup signals from the second image pickup portions to configure the second images (image signals). Further, the image configuring portion 20 arranges the configured first image and second images so that the images mutually adjoin. For example, the image configuring portion 20 configures an image in which the first image and the plurality of second images are arranged at a center and at a plurality of angle positions in a circumferential direction of the first image (in the example of FIG. 1, two equally divided positions in the circumferential direction), respectively, corresponding to the respective field-of-view directions of the image pickup portions 11 to 13 based on the first image and the second images.

More specifically, the image configuring portion 20 is configured including, for example, a frame buffer, and the image configuring portion 20 configures an image corresponding to one frame, which is constituted by respective pixels of the first image and respective pixels of the second images, by storing image pickup signals sequentially inputted from the image pickup portions 11 to 13, for example, in pixels into addresses corresponding to pixel positions in the frame buffer.

The illumination control portion 21 adjusts respective amounts of light of the illumination portions 15 to 17 individually to cause the illumination portions 15 to 17 to emit light. That is, the illumination control portion 21 controls the amount of light of the first illumination portion and the amount of light of the second illumination portions independently.

The luminance detecting portion 22 detects each of luminance of the first image and luminance of the second images. More specifically, the luminance detecting portion 22 detects luminance of each of the pixels constituting the first image and the second images, and, furthermore, detects luminances of a plurality of areas Re obtained by dividing the images as described later.

The luminance control portion 23 adjusts the luminance of at least one of the first image and the second images so that a luminance difference between adjoining parts of the first and second images adjoiningly arranged is equal to or smaller than a predetermined threshold (a luminance difference threshold).

The threshold storing portion 24 nonvolatilely stores the threshold described above. The threshold storing portion 24 is adapted to further store a lower limit luminance Ad (see FIG. 5) and an upper limit luminance Au (see FIG. 3) also as described later.

The image outputting portion 25 outputs a display signal in which the first image and the second images are adjoiningly arranged, based on the image for which luminance adjustment has been performed by the luminance control portion 23.

Receiving the display signal outputted from the image outputting portion 25, the monitor 3, which is a display portion, displays the image. More specifically, on a screen of the monitor 3, a forward image 31 based on an image pickup signal obtained from the image pickup portion 11 (based on the first image), a right lateral image 32 based on an image pickup signal obtained from the image pickup portion 12, and a left lateral image 33 based on an image pickup signal obtained from the image pickup portion 13 (the right lateral image 32 and the left lateral image 33 are based on the second images, respectively) are arranged and displayed at a center, on a right side of the forward image 31, and on a left side of the forward image 31, respectively.

That is, the image configuring portion 20 is adapted to configure an image so that the first image and the second images are adjoiningly arranged in a same screen. Arrangement of each of the images 31 to 33 seen from an observer corresponds to each field-of-view direction seen from the endoscope 1, and, image configuration is realized as if observation were performed by one super-wide angle camera.

Note that, in the example shown in FIG. 1, non-image areas where the images acquired by the image pickup portions 11 to 13 are not displayed (areas constituted by non-image pixels which do not constitute none of the first image and the second images) are displayed between the forward image 31 and the right lateral image 32, between the forward image 31 and the left lateral image 33, and around the forward image 31, the right lateral image 32 and the left lateral image 33.

Further, in the example shown in FIG. 1, the forward image 31, the right lateral image 32 and the left lateral image 33 are displayed on one monitor 3, the respective images may be displayed on separate monitors. That is, the image outputting portion 25 outputs the first image and the second images as either a single display signal for displaying the images on one monitor 3 or a plurality of display signals for displaying the images on a plurality of monitors 3.

Next, a luminance adjustment process in the endoscope system of the present invention will be described along flowcharts in FIGS. 6 to 8 with reference to FIGS. 2 to 5.

The endoscope system of the present embodiment is characterized in performing processes shown in flowcharts of FIGS. 6 to 8 not as processes to be executed for an endoscopic image acquired in advance, later separately, but as processes for performing luminance adjustment for an endoscopic image acquired by the endoscope 1 in real time by the video processor 2.

Figure 6:
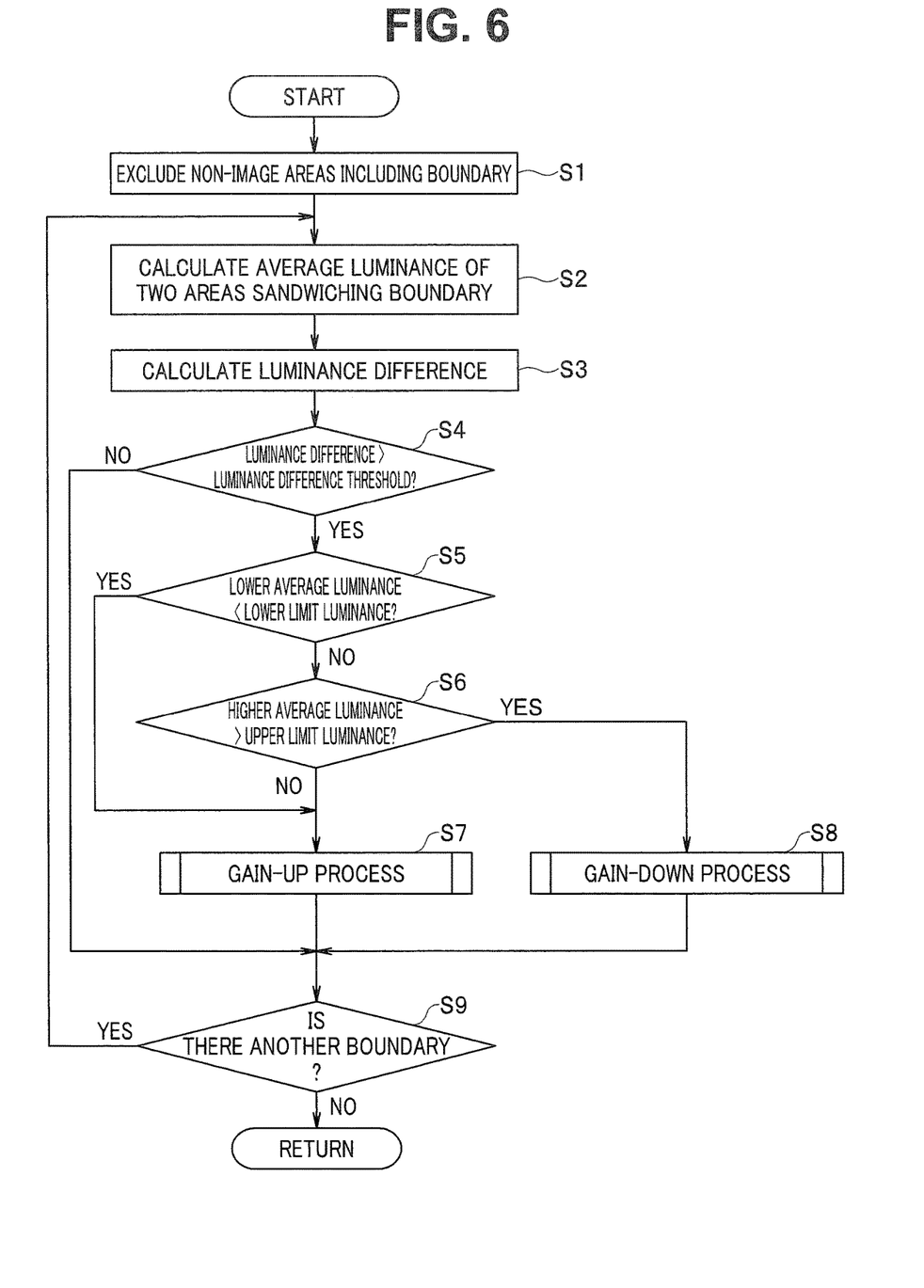
FIG. 6 is a flowchart showing a luminance adjustment process of the endoscope system in the above first embodiment.

First, FIG. 6 is a flowchart showing the luminance adjustment process of the endoscope system.

When the process is entered from a main process not shown, non-image areas including boundary areas among images are excluded from a processing target (step S1). Thereby, the luminance control portion 23 does not perform luminance adjustment for non-image pixels which constitute none of the first image and the second images (for example, non-image pixels in the boundary areas among the images).

Next, for example, the luminance detecting portion 22 divides each of the first image and the second images into a plurality of areas Re (see FIG. 1) and calculates average luminance of each divided area Re for each area Re (step S2). Here, the average luminance is obtained by averaging luminances of pixels in the area Re. By the process, average luminances of two areas Re adjoining each other sandwiching a boundary.

Figure 2:
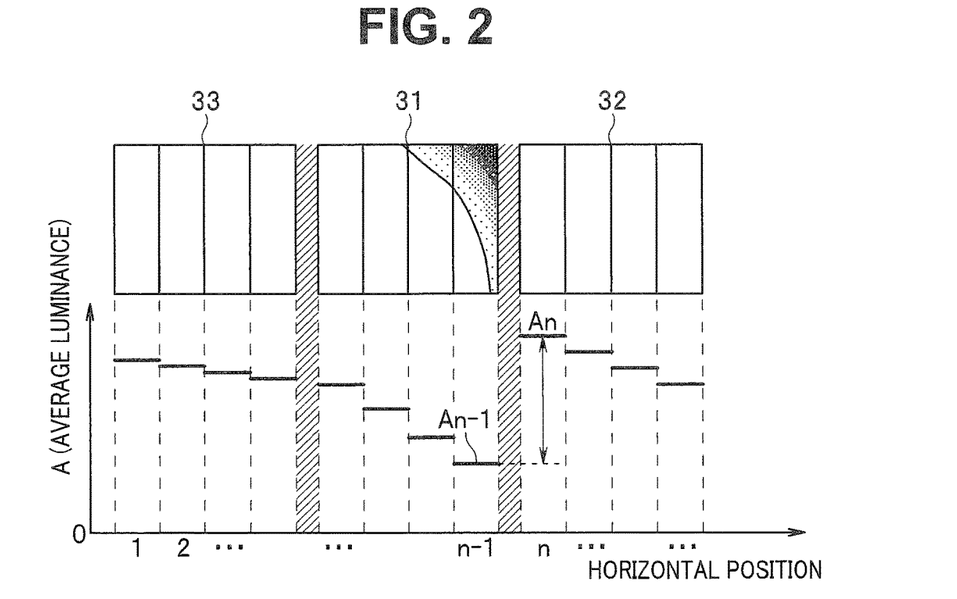
FIG. 2 is a diagram showing an example of luminance distribution of a plurality of images with a plurality of fields of view in the above first embodiment.

Here, FIG. 2 is a diagram showing an example of luminance distribution of a plurality of images with different fields of view.

First, the area Re is constituted by one or more pixels (therefore, it is possible to configure the area Re with one pixel). Then, the luminance detecting portion 22 in the present embodiment sets the area Re as an area constituted by a plurality of pixels and, for example, a longitudinally rectangular area obtained by plurally dividing an image (the forward image 31, the right lateral image 32 and the left lateral image 33) in a horizontal direction (see FIGS. 1, 2 and the like).

The way of dividing an image into a plurality of areas Re is not limited to the above. For example, an image may be divided into grid-like areas obtained by plurally dividing the image in horizontal and vertical directions, or may be divided into concentric shaped (for example, concentric circle-shaped or concentric polygon-shaped) areas obtained by plurally dividing the image in a radial direction, or other division methods may be adopted.

It is assumed that, as a result of the luminance detecting portion 22 calculating an average luminance A of each area Re, luminance distribution of the images is as shown in FIG. 2.

The luminance distribution shown in FIG. 2 shows a state that the amount of light of the illumination portion 16 is increased to cause the right lateral image 32 to be bright in a luminal shaped subject because the endoscope comes close to, for example, a left side wall, and a distance to a right side wall becomes far, so that the right lateral image 32 becomes dark. That is, a large luminance difference between two areas Re adjoining each other sandwiching a boundary as shown in FIG. 2 occurs, for example, by performing light amount control of the illumination portions 15 to 17 by the illumination control portion 21. Therefore, the luminance control portion 23 performs luminance adjustment for the first image and the second images acquired after the light amount control by the illumination control portion 21 is performed.

At this time, adjoining parts sandwiching the boundary between the forward image 31 and the right lateral image 32, more specifically, between an average luminance $A_{n-1}$ of the (n−1)-th area Re on the forward image 31 side and an average luminance $A_n$ of the n-th area Re in the right lateral image 32, a large luminance difference occurs. Here, numbers 1, 2, . . . , (n−1), n, . . . indicating horizontal positions of the areas Re are sequential numbers from the left lateral image 33 to the right lateral image 32 via the forward image 31.

The luminance control portion 23 calculates a luminance difference $|A_n-A_{n-1}|$ between the two areas Re adjoining each other sandwiching the boundary (step S3) and judges whether or not the calculated luminance difference $|A_n-A_{n-1}|$ is larger than the threshold (luminance difference threshold) read out from the threshold storing portion 24 (step S4).

Here, if it is judged that the luminance difference is larger than the threshold, the luminance control portion 23 further judges whether a lower average luminance is smaller than the predetermined lower limit luminance Ad (see FIG. 5) or not (step S5), the lower average luminance being the average luminance $A_{n-1}$ in the example shown in FIG. 2 because the average luminance $A_{n-1}$ is lower than the average luminance $A_n$. Here, the lower limit luminance Ad is a luminance showing a lower limit of a luminance range appropriate for observing an image to perform diagnosis.

Here, if it is judged that the lower average luminance is equal to or larger than the lower limit luminance Ad, then a higher average luminance, the average luminance $A_n$ in the example shown in FIG. 2 is larger than the predetermined upper luminance Au (see FIG. 3) or not (step S6). Here, the upper limit luminance Au is a luminance showing an upper limit of the luminance range appropriate for observing an image to perform diagnosis.

Figure 7:
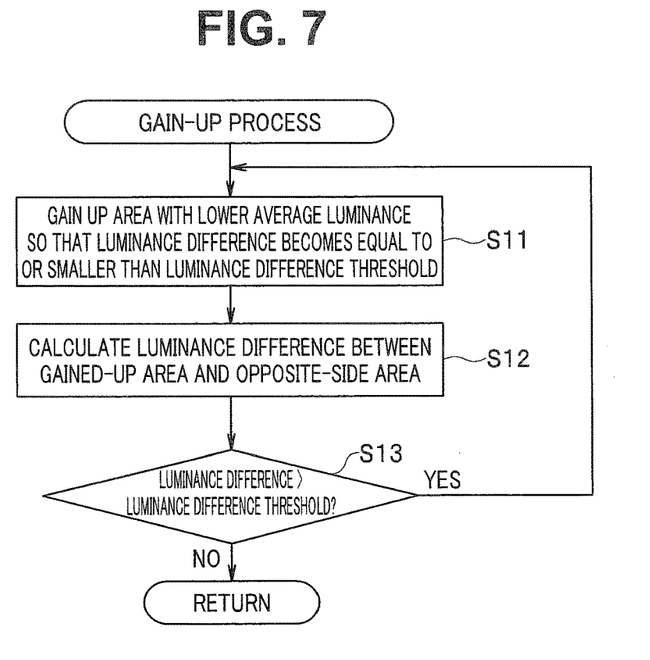
FIG. 7 is a flowchart showing details of a gain-up process at step S7 in FIG. 6 in the above first embodiment.

If it is judged at step S6 that the higher average luminance is equal to or smaller than the upper limit luminance Au or it is judged at step S5 that the lower average luminance is smaller than the lower limit luminance Ad, a gain-up process as described later with reference to FIG. 7 is performed (step S7).

Note that, though the gain-up process is performed here if it is judged that the lower average luminance is equal to or larger than the lower limit luminance Ad and that the higher average luminance is equal to or smaller than the upper limit luminance Au, a gain-down process may be performed instead.

Figure 8:
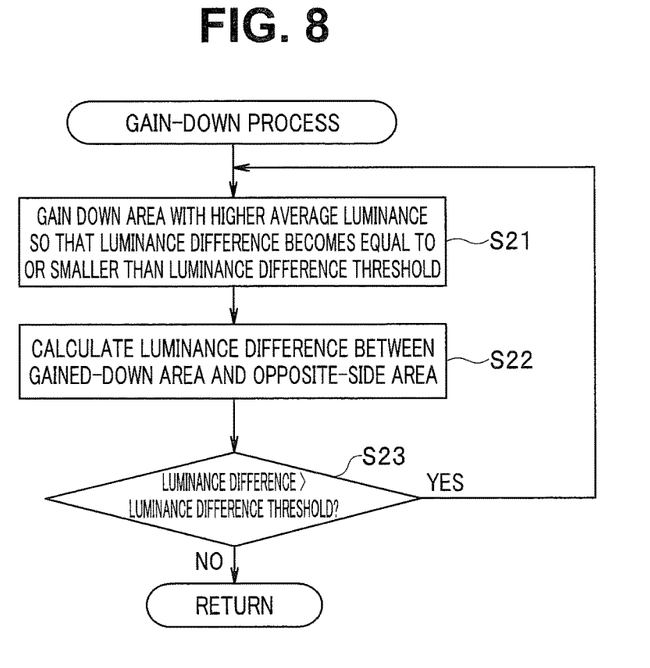
FIG. 8 is a flowchart showing details of a gain-down process at step S8 in FIG. 6 in the above first embodiment.

On the other hand, if it is judged at step S6 that the higher average luminance is larger than the upper limit luminance Au, a gain-down process as described later with reference to FIG. 8 is performed (step S8).

If it is judged at step S4 that the luminance difference $|A_n-A_{n-1}|$ is equal to or smaller than the threshold or if the process of step S7 or step S8 is performed, it is further judged whether another boundary between images further exists or not (step S9).

Here, if it is judged that another boundary further exists, the flow goes to step S2, and the process as described above is performed for areas Re sandwiching the other boundary. In the example shown in FIGS. 1 and 2, since not only the boundary between the forward image 31 and the right lateral image 32 but also a boundary between the forward image 31 and the left lateral image 33 further exists, the flow transitions to step S2.

In this way, if it is judged at step S9 that no other boundary exists, the flow returns from the process to the main process not shown.

FIG. 7 is a flowchart showing details of the gain-up process at step S7 in FIG. 6.

When the process is entered, the area Re with the lower average luminance is gained up so that the luminance difference becomes equal to or smaller than the threshold (step S11). In this way, when performing luminance adjustment by gain-up or gain-down to be described later, the luminance control portion 23 divides each of the first image and the second images into a plurality of areas Re and regards the divided areas Re as units.

Figure 5:
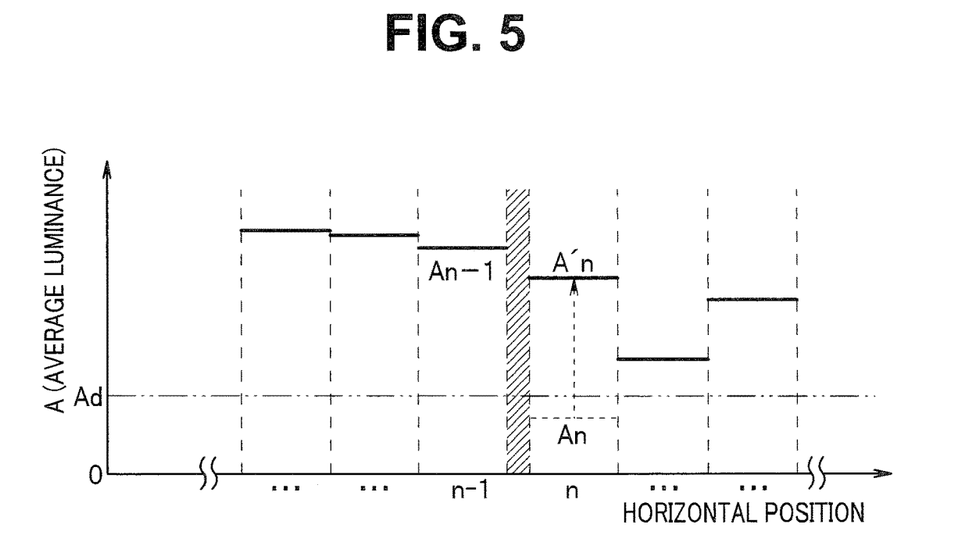
FIG. 5 is a diagram showing a state that the luminance difference between the adjoining parts of the images is suppressed by gain-up in the above first embodiment.

For example, it is assumed that luminance distribution of the images is as shown in FIG. 5. FIG. 5 is a diagram showing a state that a luminance difference between adjoining parts of images is suppressed by gain-up. The example shown in FIG. 5 is an example in which the lower average luminance $A_n$, between the average luminance $A_{n-1}$ and the average luminance $A_n$, is smaller than the lower limit luminance Ad, and it is judged at step S5 in FIG. 6 that the gain-up process of step S7 is to be performed.

In such a case, the luminance control portion 23 applies a gain larger than 1 to the lower average luminance $A_n$ so that the average luminance $A_n$ is gained up to an average luminance $A'_n$. As for the gain at this time, a specified value suitable for a product may be given, or a user may be able to set the gain.

Then, if a luminance difference $|A'_n-A_{n-1}|$ between the average luminance $A'_n$ of the gained-up area Re and the average luminance $A_{n-1}$ of the adjoining area Re on an opposite side beyond the boundary is not equal to or smaller than the threshold, a gain larger than 1 is further applied to the average luminance $A'_n$. Such a process is repeated as necessary so that the luminance difference $|A'_n-A_{n-1}|$ becomes equal to or smaller than the threshold. Note that, though a gain-up method of applying a gain larger than 1 to a lower average luminance a plurality of times until a luminance difference becomes equal to or smaller than a threshold is used here, the present invention is not limited to the method, and an arbitrary gain-up method may be appropriately used.

Even if the luminance difference $|A'_n-A_{n-1}|$ of the two adjoining areas Re sandwiching the boundary is caused to be equal to or smaller than the threshold, there is a possibility that a luminance difference $|A_{n+1}-A'_n|$ between the average luminance $A'_n$ of the area Re for which luminance adjustment has been performed and an average luminance $A_{n+1}$ of an area Re adjoining a side opposite to the boundary of the above area Re is larger than the threshold.

Therefore, the luminance difference |An+1−A'n| between the gained-up n-th area Re and the (n+1)-th area Re adjoining the side opposite to the boundary is calculated (step S12).

Then, it is judged whether the calculated luminance difference |An+1−A'n| is larger than the threshold or not (step S13).

Here, if it is judged that the luminance difference |An+1−A'n| is larger than the threshold, the flow goes to step S11, and the process as described above is performed.

Then, if it is judged at step S13 that a luminance difference calculated after performing luminance adjustment sequentially for the areas Re, from the area Re adjoining the boundary becomes equal to or smaller than the threshold, the flow returns from the process to the process shown in FIG. 6.

Next, FIG. 8 is a flowchart showing details of the gain-down process at step S8 in FIG. 6.

When the process is entered, the area Re with the higher average luminance is gained down so that the luminance difference becomes equal to or smaller than the threshold (step S21).

Figure 3:
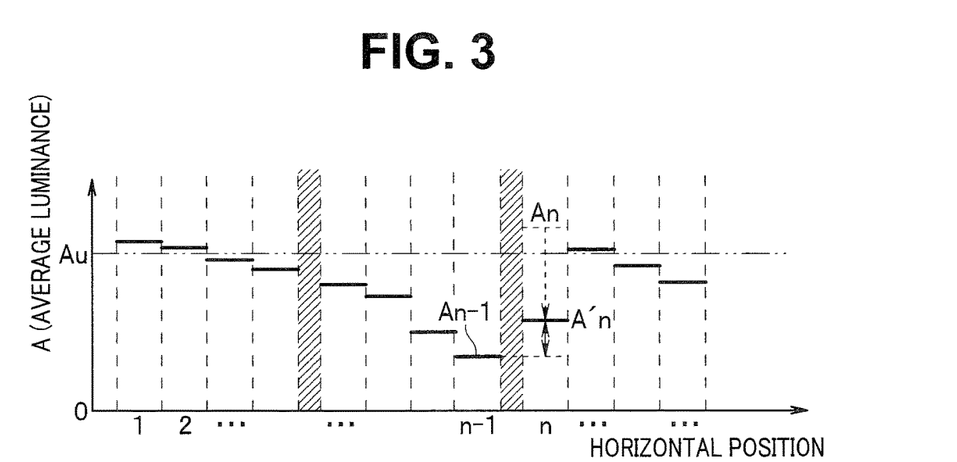
FIG. 3 is a diagram showing a state that a luminance difference between adjoining parts of images is suppressed by gain-down in the above first embodiment.

For example, it is assumed that luminance distribution of the images is as shown in FIG. 3. FIG. 3 is a diagram showing a state that a luminance difference between adjoining parts of images is suppressed by gain-down. The example shown in FIG. 3 is an example in which the higher average luminance An, between the average luminance An−1 and the average luminance An, is larger than the upper limit luminance Au, and it is judged at step S6 in FIG. 6 that the gain-down process of step S8 is to be performed.

In such a case, the luminance control portion 23 applies a gain smaller than 1 to the higher average luminance An so that the average luminance An is gained down to the average luminance A'n. As for the gain at this time also, a specified value suitable for a product may be given, or a user may be able to set the gain, similarly as described above, Then, if a luminance difference |A'n−An−1| between the average luminance A'n of the gained-down area Re and the average luminance An−1 of the adjoining area Re on an opposite side beyond the boundary is not equal to or smaller than the threshold, a gain smaller than 1 is further applied to the average luminance A'n. Such a process is repeated as necessary so that the luminance difference |A'n−An−1| becomes equal to or smaller than the threshold. Note that, though a gain-down method of applying a gain smaller than 1 to a higher average luminance a plurality of times until a luminance difference becomes equal to or smaller than a threshold is used here, the gain down method is not limited to the method, and an arbitrary gain-down method may be appropriately used.

Then, similarly as described above, the luminance difference |An+1−A'n| between the gained-down n-th area Re and the (n+1)-th area Re adjoining the side opposite to the boundary is calculated similarly (step S22), and it is judged whether the calculated luminance difference |An+1−A'n| is larger than the threshold or not (step S23).

Here, if it is judged that the luminance difference |An+1−A'n| is larger than the threshold, the flow goes to step S21, and the process as described above is performed.

Figure 4:
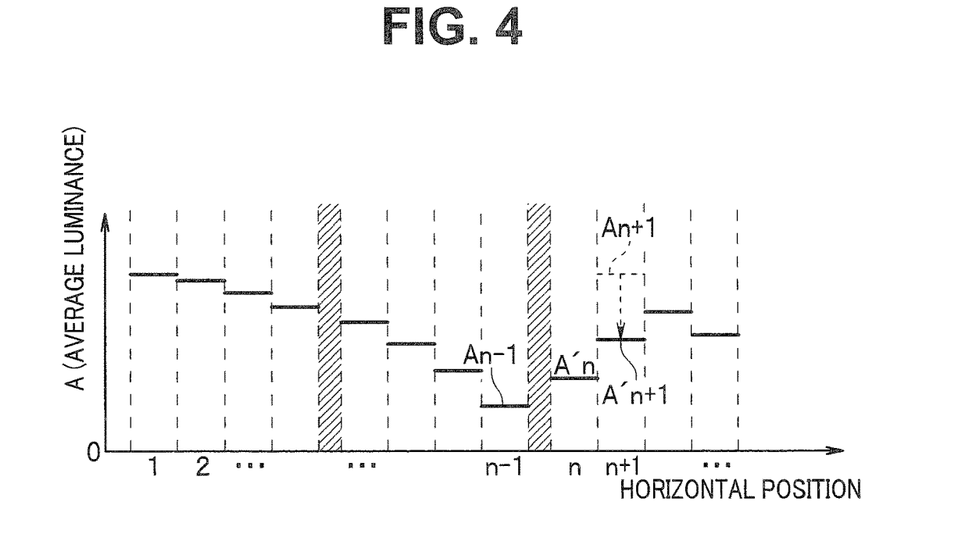
FIG. 4 is a diagram showing a state that a luminance difference of a part further adjoining the adjoining parts of the images is suppressed by gain-down in the above first embodiment.

More specifically, as shown in FIGS. 3 and 4, if the luminance difference between the average luminance A'n after luminance adjustment and the average luminance An+1 of the area Re adjoining the side opposite to the boundary becomes larger than the threshold, the average luminance An+1 is gained down to an average luminance A'n+1 so that a luminance difference |A'n+1−A'n| after luminance adjustment becomes equal to or smaller than the threshold. Here, FIG. 4 is a diagram showing a state that a luminance difference of a part further adjoining the adjoining parts of the images is suppressed by gain-down.

Then, if it is judged at step S23 that a luminance difference calculated after performing luminance adjustment sequentially for the areas Re, from the area Re adjoining the boundary becomes equal to or smaller than the threshold, the flow returns from the process to the process shown in FIG. 6.

Note that, though it is judged based on an average luminance of pixels in an area Re whether or not to perform the luminance adjustment process by the luminance control portion 23 in the above description, the judgment may be performed based on a weighted average luminance obtained by weighting luminances of the pixels in an area Re instead. For example, at time of observing an image, a subject located at a central part in a vertical direction of the image is more important than a subject located at an upper end or lower end of the image. Therefore, in a case of weighting and arithmetic averaging luminances of pixels in an area Re, it is recommended, for example, to weight pixels at the central part in the vertical direction much and weight pixels at upper and lower end portions little.

Further, it is possible to make the judgment that the luminance adjustment process by the luminance control portion 23 is to be performed if, when a luminance difference for each pair of pixels facing each other sandwiching a boundary is calculated, a rate of such pixel pairs that the luminance difference is larger than a threshold is equal to or larger than a predetermined rate.

Furthermore, though either the gain-up process or the gain-down process is performed for one boundary in the process shown in FIG. 6, such a process may be performed that an area Re with a lower average luminance and an area Re with a higher average luminance sandwiching a boundary are gained up and gained down, respectively, if it does not matter that the process is a little complicated.

According to the first embodiment as described above, in order that a luminance difference between adjoining parts of a first image and a second image arranged adjoining each other becomes equal to or smaller than a predetermined threshold, luminance of at least one of the first image and the second image is adjusted. Therefore, it is possible to suppress a luminance difference between adjoining parts of a plurality of images with different fields of view to increase visibility.

Further, since luminance adjustment is performed for areas Re obtained by dividing images, as units, luminance differences inside the areas are maintained, and shadows and solidity inside the areas Re can be maintained.

Furthermore, since a luminance difference based on an average luminance is calculated and compared with a threshold to perform luminance adjustment, it is possible to appropriately grasp a luminance difference between adjoining areas Re to perform luminance adjustment.

Further, luminance adjustment is performed by either gain-up or gain-down, it is possible to reduce a luminance difference by a relatively easy process.

Further, luminance adjustment is successively performed for an area Re adjoining a side opposite to a boundary of an area Re for which luminance adjustment has been performed, it becomes possible to observe an image with natural luminance distribution in which a large luminance difference in the image is corrected as a whole.

For example, in a case of performing gain-down prior to gain-up, a bright part close to whiteout can be observed with more appropriate brightness which makes it easy to see the bright part.

Further, in a case of performing gain-up prior to gain-down, it becomes possible to observe a dark part with a more appropriate brightness which makes it easy to see the dark part.

Since luminance adjustment is not performed for non-image pixels, the non-image pixels (for example, a part between images and a part around an image, which is an outside the image) are maintained at a predetermined luminance value, and the luminance value of the non-image pixels does not change for each image. Therefore, an image easy to see is obtained.

In a case of dividing images into longitudinally rectangular areas Re, it is possible to, when arranging rectangular images in a horizontal direction to make it possible to observe a wide angle image, favorably reduce luminance differences among the images with different fields of view.

In a case of dividing images into grid-like areas Re, it is furthermore possible to reduce luminance differences which occur in a vertical direction also.

On the other hand, in a case of dividing images into concentric areas Re, it is possible to, when acquiring a plurality of concentric images having different diameters to make it possible to observe a wide angle image, favorably reduce luminance differences among the images.

Since luminance adjustment is performed for a first image and second images acquired after performing amount-of-light control by the illumination control portion 21, an image for which average luminance for each field of view is optimized is targeted by luminance adjustment, and it is possible to suppress decrease in contrast and suppress amplification of noise also.

Since the image configuring portion 20 configures an image in which a first image and second images are adjoiningly arranged, it becomes possible to observe images of a plurality fields of view at a wide angle.

If the image outputting portion 25 outputs a single display signal, the first image and the second images can be displayed on one monitor 3 and observed. Further, if the image outputting portion 25 outputs a plurality of display signals, the first image and the second images can be displayed on a plurality of monitors 3 and observed, respectively.

Since images of a forward field of view and a lateral field of view of the insertion portion 1a are acquired, it is possible to realize a super-wide angle endoscope without using an expensive, large-sized super-wide angle lens.

Since the second subject image acquiring portions arranged at a plurality of angle positions in the circumferential direction of the insertion portion 1a acquire a plurality of second image pickup signals, and the image configuring portion 20 configures such an image that a first image based on a first image pickup signal and a plurality of second images based on the plurality of second image pickup signals are arranged at a center and at a plurality of angle positions in a circumferential direction of the first image (in the example of FIG. 1, the two equally divided positions in the circumferential direction), respectively, it becomes possible to observe an image corresponding to a field-of-view direction at time of image pickup.

In the configuration in which the first image pickup portion and the second image pickup portions are separate bodies, as shown in FIG. 1, it is possible to acquire image pickup signals of a plurality of field-of-view directions.

Second Embodiment

Figure 9:
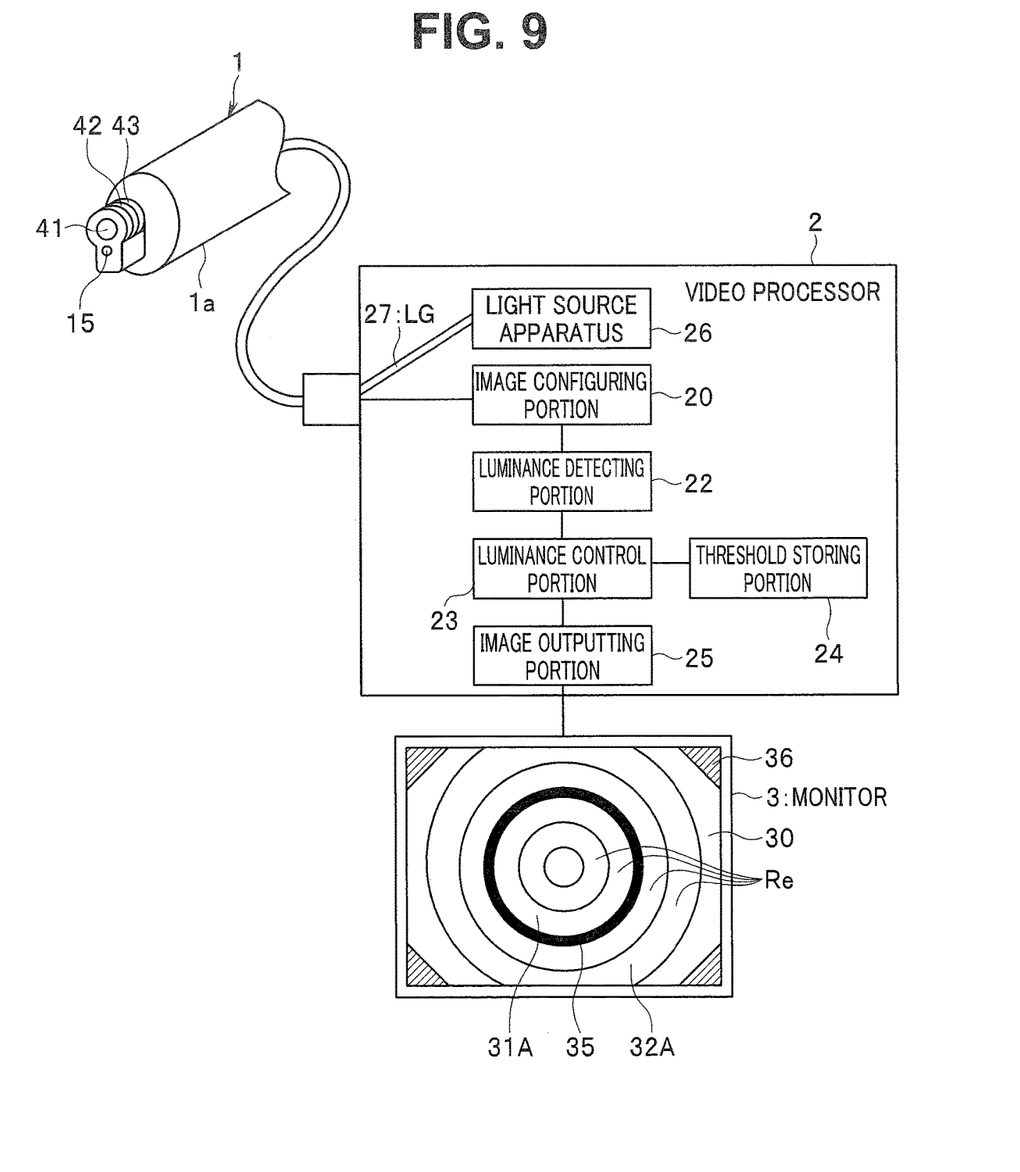
FIG. 9 is a diagram showing a configuration an endoscope system in a second embodiment of the present invention.

FIG. 9 shows a second embodiment of the present invention and is a diagram showing a configuration of an endoscope system. In the second embodiment, portions similar to the positions of the first embodiment described above will be given same reference numerals, and description of the portions will be appropriately omitted. Description will be made mainly on different points.

In the present embodiment, the configuration of an image pickup system of the endoscope 1 is changed, and a light source apparatus 26 is provided in the video processor 2 instead of providing the endoscope 1 with a light source such as an LED.

First, the distal end portion of the insertion portion 1a of the endoscope 1 is provided with a forward optical system 41 configured to acquire an optical image in a forward direction along the longitudinal direction of the insertion portion 1a (an image of a field of view of an area which includes a forward direction in a subject) and the illumination portion 15 configured to radiate light to a field-of-view range of the forward optical system 41.

A circumferential surface portion in a vicinity of a proximal end side of the forward optical system 41 and the illumination portion 15 is provided with a lateral optical system 42 configured to acquire an optical image (an image of a field of view of an area which includes a lateral direction different from the forward direction in the same subject) of a predetermined angle range in a circumferential direction (if the predetermined angle range is 360°, an entire circumference in the circumferential direction) in the lateral direction crossing the longitudinal direction of the insertion portion 1a, and an illumination portion 43 configured to radiate light to a field of view of the lateral optical system 42.

Here, the forward optical system 41 and the lateral optical system 42 may be configured as a composite optical system configured to transmit and acquire a forward optical image, and reflect and acquire an optical image of a predetermined angle range in a lateral circumferential direction.

The forward optical image by the forward optical system 41 and the lateral (circumferential direction) optical image by the lateral optical system 42 are formed, for example, on different image pickup areas on a single image pickup device.

Therefore, in the present embodiment, the first subject image acquiring portion is configured with the forward optical system 41 and an image pickup area for picking up an optical image in a forward direction of the image pickup device, and is arranged in the distal end portion of the insertion portion 1a facing forward.

Further, the second subject image acquiring portion is configured with the lateral optical system 42 and an image pickup area for picking up an optical image in a lateral circumferential direction of the image pickup device, and arranged on a circumferential surface portion of the insertion portion 1a so as to be capable of picking up a subject image of a predetermined angle range in a circumferential direction.

Therefore, the first subject image acquiring portion and the second subject image acquiring portion share and include one image pickup portion (an image pickup device); an optical image of a subject existing in a first field of view (a first subject image) is formed on a part of the image pickup portion to generate a first image pickup signal; and an optical image of a subject existing in a second field of view (a second subject image) is formed on another part of the image pickup portion to generate a second image pickup signal.

The first and second image pickup signals generated by the image pickup device are outputted to the video processor 2 and connected to the image configuring portion 20, the luminance detecting portion 22, the luminance control portion 23 and the image outputting portion 25 which are described above (that is, the image pickup portion is electrically connected to the luminance control portion 23).

On the other hand, the video processor 2 is provided with the light source apparatus 26 configured to emit illuminating light, instead of the illumination control portion 21 of the first embodiment described above. The light emitted by the light source apparatus 26 is radiated to subjects in respective field-of-view directions from the illumination portions 15 and 43 configured including an illumination optical system, via a light guide (LG) 27.

When an image obtained from the endoscope 1 having such a configuration and processed by the video processor 2 is displayed on a screen 30 of the monitor 3, the image is, for example, as shown in FIG. 9.

First, an optical image of the forward optical system 41 is formed on a central part of the image pickup device as a circular-shaped optical image, and a first image pickup signal is generated by photoelectric conversion of the image pickup device. Based on the first image pickup signal, a circular-shaped forward image 31A is configured by the image configuring portion 20.

Further, an optical image of the lateral optical system 42 is formed as a ring-shaped optical image of a predetermined angle range (if the predetermined angle range is 360°, a ring-shaped optical image) of a ring surrounding the above-described circular-shaped optical image on the central part of the image pickup device, and a second image pickup signal is generated by photoelectric conversion of the image pickup device. Based on the second image pickup signal, for example, a ring-shaped lateral image 32A of an outer circumferential portion of the forward image 31A is configured by the image configuring portion 20.

That is, the image configuring portion 20 configures an image by configuring the forward image 31A, which is a first image, in a circular shape, and configuring the lateral image 32A, which is a second image, in a shape of a predetermined angle range of a ring surrounding the forward image 31A.

Furthermore, between the forward image 31A and the lateral image 32A, a clearance 35 is caused by the configuration, arrangement and the like of the forward optical system 41 and the lateral optical system 42. Since the clearance 35 is a dark part where an optical image of a subject is not formed, on the image pickup device, a black frame shape is presented. Therefore, the clearance 35 is a set of non-image pixels which constitute neither the first image nor the second image, and the luminance control portion 23 does not perform luminance adjustment for the clearance 35.

In general, an image pickup device is provided with a rectangular image pickup surface. Image circles of the forward optical system 41 and the lateral optical system 42 are almost circular-shaped areas smaller than the image pickup surface as shown in an image in FIG. 9. Therefore, around the lateral image 32A also, non-image areas 36 constituted by sets of non-image pixels which constitute neither the first image nor the second image are generated.

In such a configuration, the luminance detecting portion 22 and the luminance control portion 23 plurally divide the forward image 31A and the lateral image 32A in a radial direction, for example, into concentric circle-shaped (not limited to "concentric circle-shaped" but "concentric polygon-shaped" and the like are also possible) areas Re, and perform detection of average luminance and luminance adjustment for each area Re as a unit.

According to the second embodiment as described above, effects almost similar to the effects of the first embodiment described above are provided, and, in the case where a first image pickup signal of a first subject image of a forward direction of the insertion portion 1a and a second image pickup signal of a second subject image of a predetermined angle range in the circumferential direction of the insertion portion 1a are acquired, and the image configuring portion 20 configures an image signal (an image) by configuring a first image in a circular shape and configuring a second image in a shape of a predetermined angle range of a ring surrounding the first image also, it becomes possible to observe the image corresponding to a field-of-view direction at time of image pickup.

Further, if the configuration in which the first subject image acquiring portion and the second subject image acquiring portion share one image pickup portion is adopted, it is possible to effectively reduce the diameter and weight of the distal end portion of an endoscope.

Furthermore, in the case of performing, for boundary parts of a first image (the forward image 31A) and a second image (the lateral image 32A), luminance adjustment for at least one of the first image and the second image, a process may be performed in which an image (an image signal) is resolved to cut out an area for a first image and an area for a second image, luminance adjustment similar to that described in the first embodiment is performed for each area, and the processed first and second images are combined to be returned to one image like the original image.

Third Embodiment

Figure 10:
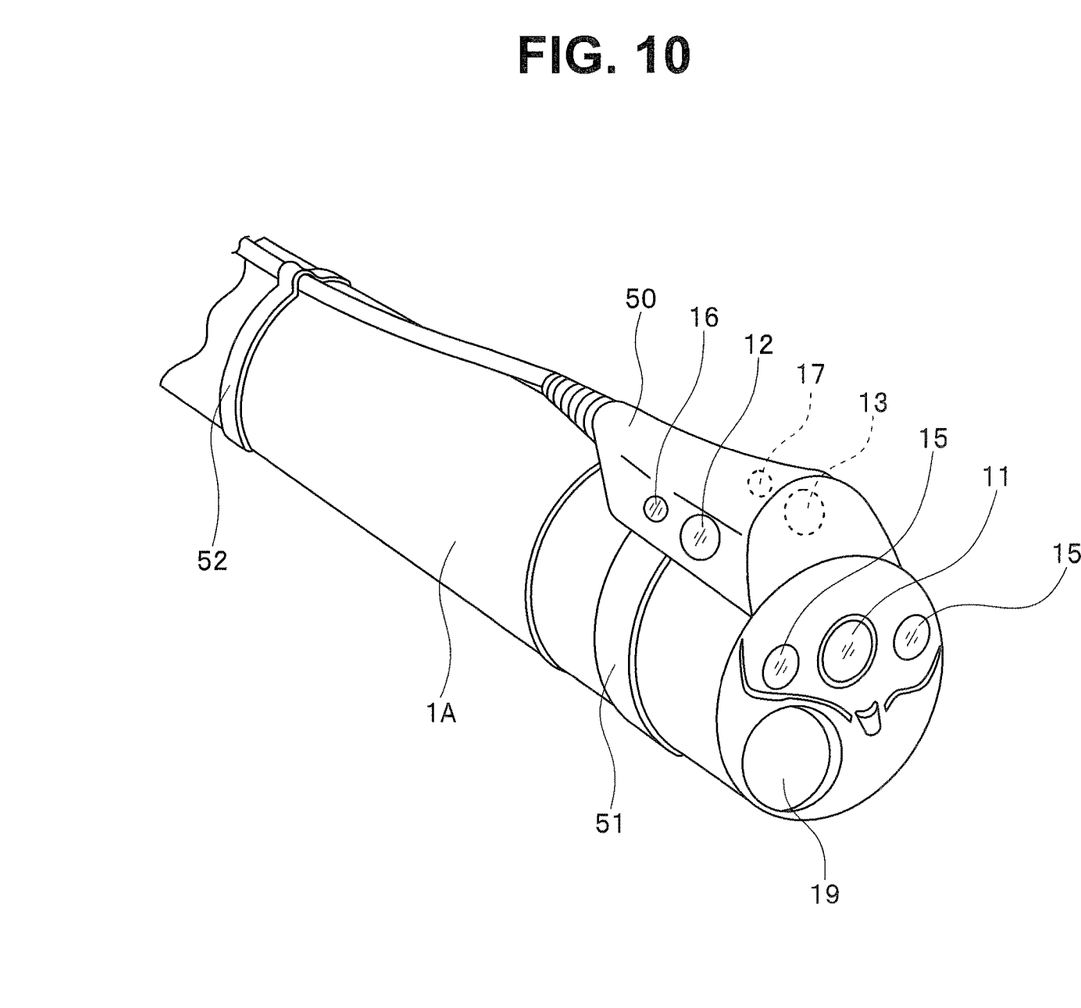
FIG. 10 is a perspective view partially showing a configuration of an endoscope in a state of being equipped with a lateral image acquiring unit in a third embodiment of the present invention.
Figure 11:
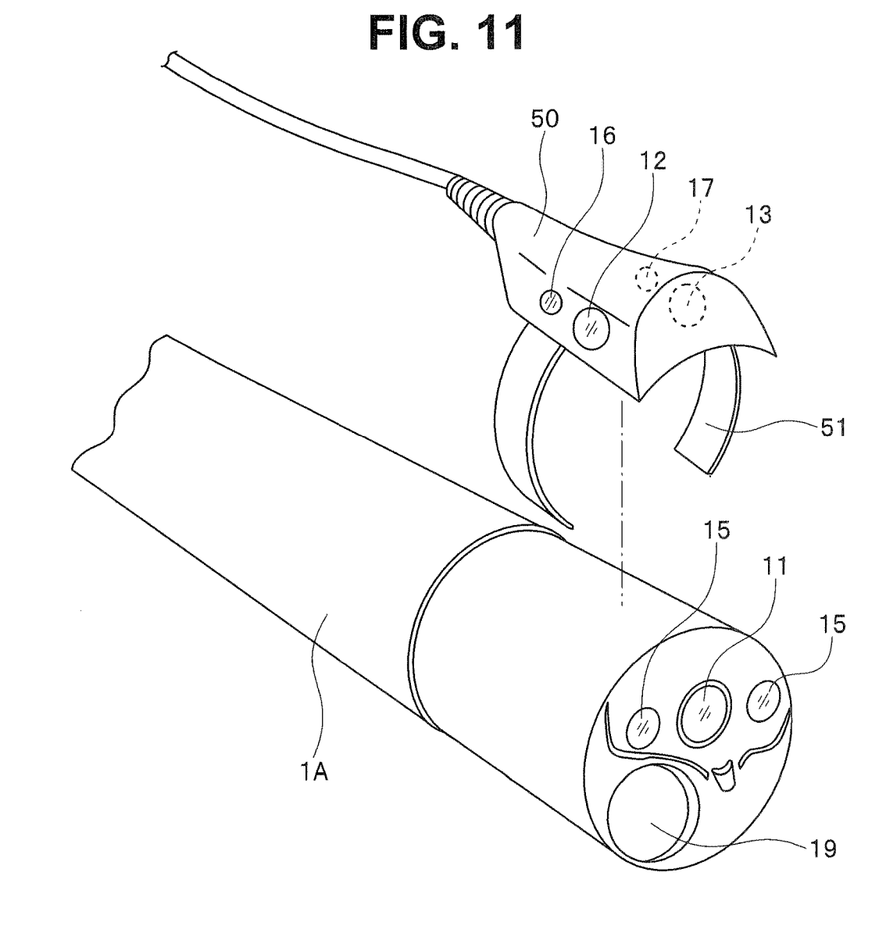
FIG. 11 is a perspective view partially showing the configuration of the endoscope in a state of the lateral image acquiring unit being removed in the above third embodiment.

FIGS. 10 and 11 show a third embodiment of the present invention. FIG. 10 is a perspective view partially showing a configuration of an endoscope in a state of being equipped with a lateral image acquiring unit 50. FIG. 11 is a perspective view partially showing the configuration of the endoscope in a state of the lateral image acquiring unit 50 being removed.

In the third embodiment, portions similar to the portions of the first and second embodiments described above will be given same reference numerals, and description of the portions will be appropriately omitted. Description will be made mainly on different points.

The endoscope of the present embodiment is provided with an endoscope body 1A and the lateral image acquiring unit 50 as shown in FIGS. 15 and 16.

Here, the endoscope body 1A is provided with the image pickup portion 11 configured to acquire a first image pickup signal of the forward image 31, the illumination portion 15 configured to radiate light to a forward direction, which is a range of image pickup by the image pickup portion 11, and a forceps channel 19 for inserting a treatment instrument such as a forceps, and the endoscope body 1A can be also used as a general front-view type endoscope.

The lateral image acquiring unit 50 is configured being attachable to and detachable from the endoscope body 1A.

The lateral image acquiring unit 50 is provided with the image pickup portion 12 configured to acquire a second image pickup signal of the right lateral image 32, the illumination portion 16 configured to radiate light to a right lateral direction which is a range of image pickup by the image pickup portion 12, the image pickup portion 13 configured to acquire a second image pickup signal of the left lateral image 33, the illumination portion 17 configured to radiate light to a left lateral direction which is a range of image pickup by the image pickup portion 13, a fitted arm portion 51 for attaching the lateral image acquiring unit 50 to the endoscope body 1A by being fitted to the endoscope body 1A, and a fitting band 52 for fitting a cord on a proximal end side of the lateral image acquiring unit 50 to the endoscope body 1A.

To the endoscope configured by combining the endoscope body 1A as described above with the lateral-viewing lateral image acquiring unit 50 which is attachable to and detachable from the endoscope body 1A, luminance adjustment for reducing a luminance difference between images similar to that of each embodiment described above is also applicable.

Effects almost similar to the effects of the first and second embodiments described above can be also provided by using the endoscope of the third embodiment as described above, and it becomes possible to use only the endoscope body 1A as a front-view type endoscope as necessary. Otherwise, by combining the lateral image acquiring unit 50 with a general front-view type endoscope, it becomes possible to realize a wide angle endoscope capable of observing both of a forward field of view and a lateral field of view.

Note that, though an example in which the first subject image acquiring portion and the second subject image acquiring portion are provided in the endoscope 1 and an example in which the first subject image acquiring portion and the second subject image acquiring portion are provided in the endoscope body 1A and the lateral image acquiring unit 50, respectively, have been described above, the present invention is not limited to the examples. Though each of the first subject image acquiring portion and the second subject image acquiring portion includes, for example, the image pickup optical system and the image pickup device, it is also possible to arrange the image pickup optical system between them in the endoscope 1 (or the endoscope body 1A and the lateral image acquiring unit 50) and arrange the image pickup device in the video processor 2. In this case, an optical image formed by the image pickup optical system can be transmitted to the image pickup device in the video processor 2 via a transmission optical system or the like.

Though description has been made above mainly on an endoscope system, an operation method for causing the endoscope system to operate as described above is also possible. A process program for causing a computer to cause the endoscope system as described above, a non-temporary computer-readable recording medium for recording the process program, and the like are also possible.

According to the configuration of each embodiment described above, in an endoscope system, especially in an endoscope system including a wide angle endoscope having a front-view observation optical system and a lateral-view observation optical system, it is possible to observe an image with a high visibility in which brightness differences between adjoining parts of a plurality of images (image signals) with different fields of view are suppressed.

Note that the present invention is not limited to the above embodiments as they are, and the components can be modified and embodied within a range not departing from spirit of the invention at a stage of practicing the embodiments. Further, aspects of various inventions can be formed by appropriately combining a plurality of components disclosed in the above embodiments. For example, some components may be deleted from all the components shown in the embodiments. Furthermore, components among different embodiments may be appropriately combined. Thus, various modifications and applications are, of course, possible within a range not departing from the spirit of the invention.

What is claimed is:

1. An endoscope system comprising:
a processor comprising hardware, wherein the processor is configured to:
configure a first image and a second image so as to be arranged adjoining each other based on image pickup signals corresponding to different areas in a same subject;
divide each of the first image and the second image arranged adjoining each other into a plurality of areas including a first area of the first image and a second area of the second image, wherein the first area and the second area adjoin each other while sandwiching a boundary between the first image and the second image;
calculate an average luminance of each of the first area of the first image and the second area of the second image;
calculate a luminance difference between the first area of the first image and the second area of the second image based on the average luminance of the first area of the first image and the average luminance of the second area of the second image;
compare the luminance difference with a predetermined threshold;
adjust a luminance of at least one of the first image and the second image by performing one of:
gain-up to increase a luminance of an area with a lower average luminance, between the first area of the first image and the second area of the second image; and
gain-down to decrease a luminance of an area with a higher average luminance, between the first area of the first image and the second area of the second image, so that the luminance difference between the first area of the first image and the second area of the second image becomes equal to or smaller than the threshold; and
in the first image or the second image for which luminance adjustment is performed, sequentially perform luminance adjustment for an area adjoining a side opposite to the boundary of the area for which the luminance adjustment is performed.

2. The endoscope system according to claim 1, wherein the processor is configured to perform the gain-down if the luminance of the area with the lower average luminance between the two areas adjoining each other sandwiching the boundary between the first image and the second image is equal to or larger than a predetermined lower limit luminance and the luminance of the area with the higher average luminance is larger than a predetermined upper limit luminance, and, otherwise, perform the gain-up.

3. The endoscope system according to claim 1, wherein the processor is configured to not perform the luminance adjustment for non-image pixels that constitute neither the first image nor the second image.

4. The endoscope system according to claim 1, wherein the processor is configured to divide the first image and the second image into the plurality of areas in longitudinally rectangular shapes obtained by plurally dividing the images in a horizontal direction, grid-like shapes obtained by plurally dividing the images in the horizontal direction and a vertical direction or concentric shapes obtained by plurally dividing the images in a radial direction.

5. The endoscope system according to claim 1, further comprising:
   a first light source configured to radiate light to a first area in the subject; and
   a second light source configured to radiate light to a second area in the subject different from the first area;
   wherein the processor is configured to:
      control an amount of light of the first light source and an amount of light of the second light source independently; and
      perform the luminance adjustment for the first image constituted by a first image pickup signal corresponding to the first area and the second image constituted by a second image pickup signal corresponding to the second area after the amount-of-light control is performed.

6. The endoscope system according to claim 1,
   wherein the processor is configured to output a display signal based on an image in which the first image and the second image are arranged adjoining each other.

7. The endoscope system according to claim 6,
   wherein the processor is configured to output the display signal as a single display signal for displaying the first image and the second image on one display or as a plurality of display signals for displaying the images on a plurality of displays.

8. The endoscope system according to claim 6, further comprising:
   an insertion portion configured to be inserted into an inside of the subject;
   a first subject image sensor provided in the insertion portion and configured to acquire a first image pickup signal of a first subject image in a first area in the subject including a forward direction along a longitudinal direction of the insertion portion; and
   a second subject image sensor provided in the insertion portion and configured to acquire a second image pickup signal of a second subject image in a second area in the subject including a lateral direction crossing the longitudinal direction of the insertion portion, the second area being different from the first area,
   wherein the processor is configured to configure the first image based on the first image pickup signal and configure the second image based on the second image pickup signal.

9. The endoscope system according to claim 8,
   wherein the first subject image sensor is arranged in a distal end portion of the insertion portion facing forward,
   wherein the second subject image sensor is arranged facing a circumferential direction of the insertion portion, and
   wherein the processor is configured to configure the image in which the first image and the second image are arranged adjoining each other.

10. The endoscope system according to claim 9,
    wherein the second subject image sensor is arranged in plurality at a plurality of angle positions in the circumferential direction of the insertion portion and configured to acquire a plurality of second image pickup signals of the second subject image in plurality, and
    wherein the processor is configured to configure the image in which the first image based on the first image pickup signal is arranged at a center, and the plurality of second images based on the plurality of second image pickup signals are arranged at the plurality of angle positions in the circumferential direction of the first image.

11. The endoscope system according to claim 8,
    wherein the first subject image sensor is arranged in a distal end portion of the insertion portion facing forward,
    wherein the second subject image sensor is arranged on a circumferential surface portion of the insertion portion, and is configured to acquire the second image pickup signal of the second subject image of a predetermined angle range in a circumferential direction, and
    wherein the processor is configured to configure the image by configuring the first image in a circular shape and configure the second image in a shape of the predetermined angle range in a ring surrounding the first image.

12. The endoscope system according to claim 6, further comprising:
    an insertion portion configured to be inserted into an inside of the subject;
    a first subject image sensor provided in the insertion portion and configured to acquire a first image pickup signal of a first subject image from a first area in the subject; and
    a second subject image sensor provided in the insertion portion and configured to acquire a second image pickup signal of a second subject image from a second area in the subject different from the first area,
    wherein the processor is configured to configure the first image based on the first image pickup signal and configure the second image based on the second image pickup signal,
    wherein the first subject image sensor is configured to perform photoelectric conversion of the first subject image to generate the first image pickup signal,
    wherein the second subject image sensor is configured to perform photoelectric conversion of the second subject image to generate the second image pickup signal, the second subject image sensor being different from the first subject image sensor, and
    wherein the first subject image sensor and the second subject image sensor are electrically connected to the processor.

13. The endoscope system according to claim 6, further comprising:
    an insertion portion configured to be inserted into an inside of the subject; and
       an image sensor provided in the insertion portion and configured to acquire a first image pickup signal of a first subject image from a first area in the subject, and acquire a second image pickup signal of a second subject image from a second area in the subject different from the first area,
    wherein the processor is configured to configure the first image based on the first image pickup signal and configure the second image based on the second image pickup signal,
    wherein the first subject image is formed on a part of the image sensor to generate the first image pickup signal,
    wherein the second subject image is formed on another part of the image sensor to generate the second image pickup signal, and
    wherein the image sensor is electrically connected to the processor.

14. The endoscope system according to claim 1, further comprising:
   an insertion portion configured to be inserted into an inside of the subject;
   a light source configured to radiate light to a first area in the subject and a second area in the subject different from the first area;
   a first subject image sensor provided in the insertion portion and configured to acquire a first image pickup signal of a first subject image of the first area; and
   a second subject image sensor provided in the insertion portion and configured to acquire a second image pickup signal of a second subject image of the second area;
   wherein the processor is configured to:
      configure the first image based on the first image pickup signal and configure the second image based on the second image pickup signal; and
      detect each of the luminance of the first image and the luminance of the second image.

15. A method for operating an endoscope system comprising:
   configuring a first image and a second image so as to be arranged adjoining each other based on image pickup signals corresponding to different areas in a same subject;
   dividing each of the first image and the second image arranged adjoining each other into a plurality of areas including a first area of the first image and a second area of the second image, wherein the first area and the second area adjoin each other while sandwiching a boundary between the first image and the second image;
   calculating an average luminance of each of the first area of the first image and the second area of the second image;
   calculating a luminance difference between the first area of the first image and the second area of the second image based on the average luminance of the first area of the first image and the average luminance of the second area of the second image;
   comparing the luminance difference with a predetermined threshold;
   adjusting a luminance of at least one of the first image and the second image by performing one of:
      gain-up to increase a luminance of an area with a lower average luminance, between the first area of the first image and the second area of the second image; and
      gain-down to decrease a luminance of an area with a higher average luminance, between the first area of the first image and the second area of the second image,
   so that the luminance difference between the first area of the first image and the second area of the second image becomes equal to or smaller than the threshold; and
      in the first image or the second image for which luminance adjustment is performed, sequentially performing luminance adjustment for an area adjoining a side opposite to the boundary of the area for which the luminance adjustment is performed.

* * * * *